United States Patent [19]

Forquy

[11] Patent Number: 5,254,736

[45] Date of Patent: Oct. 19, 1993

[54] PROCESS FOR THE PREPARATION OF DISSYMMETRIC ALIPHATIC SECONDARY ALKYLAMINES

[75] Inventor: Christian Forquy, Monein, France

[73] Assignee: CECA, S.A., France

[21] Appl. No.: 920,755

[22] Filed: Jul. 28, 1992

[30] Foreign Application Priority Data

Jul. 29, 1991 [FR] France ................ 91 09615

[51] Int. Cl.$^5$ ........................................... C07C 209/60
[52] U.S. Cl. ............................................. 564/480
[58] Field of Search ......................... 504/479, 480

[56] References Cited

U.S. PATENT DOCUMENTS

| | | | |
|---|---|---|---|
| 3,223,734 | 12/1965 | Fallstad et al. | 564/480 |
| 4,206,149 | 6/1980 | Slaugh | 564/480 |
| 4,206,150 | 6/1980 | Slaugh | 564/480 |
| 4,207,263 | 10/1980 | Hoffmann et al. | 564/480 |
| 4,409,399 | 10/1983 | Swift et al. | 564/480 |
| 4,480,131 | 10/1984 | Klier et al. | 564/480 |
| 4,683,336 | 7/1987 | Blackhurst | 564/480 |
| 4,792,622 | 12/1988 | Yokota et al. | 564/480 |
| 5,002,922 | 3/1991 | Irgang et al. | 564/480 |

FOREIGN PATENT DOCUMENTS

| | | | |
|---|---|---|---|
| 34480 | 2/1981 | European Pat. Off. | 564/480 |
| 3223217 | 1/1983 | Fed. Rep. of Germany | 564/480 |
| 1595771 | 7/1970 | France | 564/480 |
| 2370029 | 6/1978 | France | 564/480 |
| 2370030 | 6/1978 | France | 564/480 |
| 2370031 | 6/1978 | France | 564/480 |
| 2405921 | 5/1979 | France | 564/480 |
| 1585480 | 3/1981 | United Kingdom | 564/480 |

OTHER PUBLICATIONS

Baiker et al., Catal. Rev. Sci. Eng., vol. 27, #4, pp. 653-657, (1985).

*Primary Examiner*—James H. Reamer

[57] ABSTRACT

The process for the preparation of aliphatic amines of general formula R-NH-R' in which R is an aliphatic residue with 10 to 22 carbon atoms and R' is an aliphatic residue with 1 to 8 carbon atoms, comprising reacting under a hydrogen pressure an alkanol with a monoalkylamine in the presence of a catalytic system constituted by a supported nickel catalyst and an alkaline carbonate, more specifically potassium carbonate.

9 Claims, No Drawings

PROCESS FOR THE PREPARATION OF DISSYMMETRIC ALIPHATIC SECONDARY ALKYLAMINES

BACKGROUND OF THE INVENTION

The present invention pertains to a process for the industrial production of dissymmetric secondary amines of general formula R—NH—R', in which R is a fatty chain and R' is a short chain aliphatic residue, more specifically a methyl.

Although industrial procedures are available for the selective preparation of primary amines $RNH_2$ or dimethylated tertiary amines $RN(CH_3)_2$, no selective process is known for the preparation of monomethylated secondary amines. "Selective" is understood to mean a procedure which produces the monomethylated secondary amine with a minimum amount of the corresponding primary amine and dimethylated tertiary amine.

The specifications for the target derivatives must obviously take into account their intended applications, which include the production of intermediate products for detergents which must have structures which are both oxyalkylated and can be quaternized to a single long aliphatic chain. Although it is possible to use distillation to separate amines with a single fatty chain from amines with two or three fatty chains, there is no convenient method for separating $RNH_2$ and $RN(CH_3)_2$ amines from secondary $RNHCH_3$ amines. The boiling points for a given alkyl chain length are very close (approximately 10° C.), and therefore since the general case in this chemistry is to start with raw materials which are cuts with alkyl chain lengths such as C12/C14, C14/C16, C16/C18 or C16/C22, separation of $RNH_2$, $RN(CH_3)_2$ and $RNHCH_3$ amines is not attainable. Thus, it is possible to tolerate a certain percentage of dialkyl or trialkyl amines, since they can be separated out by distillation, in proportions such that they do not impact the economy of the procedure. It is also possible to accept without dire consequences a reasonable level of dimethylamines, which follow along with the methylalkylamines as quaternized derivatives. Thus, the presence of monoalkylamines represents the major constraint.

Therefore, the goal comprises the following specifications for commercial dissymmetric secondary amines:

| | |
|---|---|
| $RNHCH_3$ | min. 85% |
| $RNH_2$ | max. 8% |
| $RN(CH_3)_2$ | max. 2% |
| $R_2NH + R_2NCH_3$ | max. 6% |
| $R_3N$ | max. 1% |
| Nonamine | max. 2% | which requires a procedure which is selective for secondary $RNHCH_3$ amine.

The prior art contains descriptions of many reactions and procedures for producing monomethylated secondary amines, notably:

(i) French Patent No. 1,595,771 (HENKEL) which describes the implementation of the reaction between a fatty acid and monomethylamine in the presence of a zinc-aluminum catalyst at 310° C., which nevertheless is not sufficiently selective for the monomethylated secondary amine since there is formation of at least 10% of dimethylated tertiary amine;

(ii) European Patent No. EP 34,480 (R.E. GRIGG) in which the use of noble metal hydride complexes of the type $RhH(PPh_3)_4$ makes possible the selective monomethylation, e.g., with methanol, of amines such as butylamine, pyrrolidine or cyclohexylamine without these catalysts being adapted to the industrial production of monomethylated amines;

(iii) French Patents No. 2,370,029, 2,370,030, 2,370,031 and 2,405,921, as well as U.S. Pat. Nos. 4,206,149 and 4,206,150, which describe implementation of the reaction between a fatty alcohol and monomethylamine on copper-based catalysts supported on alumina and containing at least one of the following elements: Cr, Zn, W, Re and Sn. These French patents do not report the selectivity for dimethylated primary and tertiary amines, but it is indicated that noteworthy amounts (>15% by weight) of dialkylated amines are formed. These American patents report reactions catalyzed on $Cu-Re/Al_2O_3$ and $Cu-W/Al_2O_3$, from which it can seen that it would be difficult to maintain the level of $RN(CH_3)_2$ below 2%; and (iv) the report to A. BAIKER and J. KIJENSKI (Catal. Rev.-Sci Eng. (27)4, 653–657, 1985) which showed that the reaction:

$$ROH + H_2N-CH_3 \rightarrow RHNCH_3 + H_2O$$

performed on a fixed bed of $Cu/SiO_2$ at 220° C. results in at least 3% of $RN(CH_3)_2$. The maximum yield obtain of $RNHCH_3$ was 75%.

SUMMARY OF THE INVENTION

It has now been discovered that it is possible to attain secondary $RNHCH_3$ amines via the reaction:

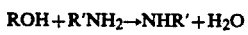
$$ROH + R'NH_2 \rightarrow NHR' + H_2O$$

in accordance with a process having a very unexpected selectivity and which is characteristically implemented in the presence of hydrogen on a particular catalytic system comprised of a nickel-based supported catalyst and an alkaline carbonate.

The system operates in the two following cases:

1. when the 10/22-carbon-atom alkyl chain is carried by the amine $RNH_2$ and methanol is made to react in accordance with the overall reaction:

$$RNH_2 + CH_3OH \rightarrow RNHCH_3 + H_2O, \text{ and}$$

2. when the 10/22-carbon-atom alkyl chain is carried by the alcohol ROH and the monomethylamine is made to react in accordance with the overall reaction:

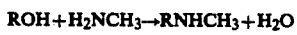
$$ROH + H_2NCH_3 \rightarrow RNHCH_3 + H_2O$$

The system also operates for the production of dissymmetric secondary amines R—NH—R' in which the short chain is a residue of 2/8 carbon atoms, in which case the short-chain reactants are an alcohol or a 2/8-carbon-atom amine, respectively.

DETAILED DESCRIPTION

The presumed amination mechanism suggests that the first step is the dehydrogenation of the alcohol. Since this reaction is governed by a thermodynamic equilibrium which is very favorable for the alcohol, it is preferable to employ a noteworthy amount of alcohol so as to generate a sufficient amount of aldehyde in equilibrium, which aldehyde reacts very quickly with the amine. Thus, in the case of reaction (1), this means maintaining a noteworthy amount of methanol in the presence of the fatty amine or, more specifically, maintaining a methanol:amine molar ratio between 15 and 30, thus working in a closed reactor with an autogenous methanol pressure reaching 27 bars at 180° C. and 30 bars at 200° C. Since a hydrogen pressure of 10 to 50 bars, preferably circa 30 bars, is also necessary so as to assure the selectivity of the reaction and maintain the catalyst's activity, the total pressure is high under the average conditions of implementing reaction (1). In addition, since the reaction is carried out in a closed reactor, it is not possible to drive out the water formed during the amination reaction, which limits the reaction speed.

In contrast, in the case of reaction (2) implemented with a fatty alcohol and momomethylamine, it is possible to place in an autoclave a noteworthy amount of fatty alcohol at a temperature higher than 180° C. under a gaseous flow composed of momomethylamine in stoichiometric excess (between 1 and 5 times the stoichiometric amount) and hydrogen circulating in the agitated solution of fatty alcohol, in the presence of the Ni/support catalytic system + $K_2CO_3$. In this case, it is possible to set the reaction pressure at the desired value and to continuously eliminate the water formed during amination which departs from the liquid phase carried by the hydrogen and the excess of monomethylamine. For all of these reasons, this mode of implementation in accordance with reaction (2) is the preferred mode of the invention, although implementation of reaction (1) is chemically equally selective.

Implementation of the procedure in accordance with the invention is generally performed by following one of the two procedures described below.

(A) From fatty amines and light alcohol (reaction 1)

The following are introduced into a 3.8-liter autoclave (1 US gallon):

(i) 500 to 1000 g of fatty amine containing 10/22 carbon atoms, (ii) 500 to 1000 g of short-chain alcohol (1 to 8 carbon atoms), (iii) 2 to 10% by weight of catalyst (percentage expressed in relation to the weight of the fatty amine), and (iv) 0.5 to 10% of potassium carbonate (percentage expressed in relation to the weight of the fatty amine).

The reactor is closed and the gaseous phase is purged several times under agitation of the liquid with a neutral gas prior to introducing 10 to 50 bars of hydrogen. The temperature of the autoclave is raised over circa one hour to 180°-200° C. under agitation of 1800 rpm for the period of time required for the almost total disappearance of the primary amine. After cooling and decompression, the liquid phase is filtered and the excess alcohol is evaporated. The evaporation residue is washed with water until the $K_2CO_3$ is eliminated.

(B) From fatty alcohol and monomethylamine (reaction 2)

The following are introduced into a 1-liter autoclave:

(i) 50 to 300 g of monomethylamine, (ii) 400 to 600 g of fatty chain alcohol containing 10/22 carbon atoms, (iii) 2 to 10% by weight of catalyst in relation to the fatty alcohol, and (iv) 0.5 to 10% of potassium carbonate $K_2CO_3$ in relation to the fatty alcohol.

The reactor is charged in accordance with the procedure described above and a circulation of hydrogen is established in the agitated reactor at a flow rate between 20 and 500 L/h, at a pressure between 10 and 50 bars, preferably at 30 bars. After a previously determined period of time, preferably after total disappearance of the fatty alcohol, the reactor is allowed to cool and is decompressed. The product is filtered. The evaporation residue is washed with hot water until elimination of the $K_2CO_3$. As described above, it is possible to introduce all of the monomethylamine at the same time, but it is much more advantageous to introduce the monomethylamine on a continuous basis during the entire duration of the operation. Similarly, all of the catalyst and the potassium carbonate can be introduced at the same time, but it also possible to introduce these substances on two or three occasions during the operation in a manner such as to make it possible to attain high heavy alcohol conversion rates.

The catalytic system which is characteristic of the invention is constituted of the combination of a supported nickel catalyst and an alkaline carbonate, more specifically potassium carbonate. A combination of this type was described in French Patent No. 2,351,088 (BASF), but the intended objective was the exclusive production of symmetrical methyl-dialkylamines $R_2NCH_3$ and the reaction to be promoted was the following:

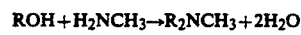

$$ROH + H_2NCH_3 \rightarrow R_2NCH_3 + 2H_2O$$

with a Ni/sodium carbonate catalyst in a weight ratio of 40:1. The catalytic systems in accordance with the present invention, which are also different from the catalysts of French Patent No. 2,351,088 in that the alkaline carbonate:nickel weight ratio is between 1:4 and 1:1, develop the reaction with a selectivity which largely eliminates the secondary amines from the tertiary amines produced. It is completely unexpected, and this is the basis of the present invention, that when a sufficient hydrogen pressure is applied to the system it also develops selectivity, but in the completely opposite direction in which the secondary amines are promoted to the detriment of the tertiary amines.

The supported nickels constitute a well known class of catalysts, which are prepared by impregnation or precipitation of nickel nitrate, or any other soluble nickel salt whose anion is not a catalytic poison, on a support such as kieselguhr, activated alumina or alumina with a high specific surface, silica or alumina silica, activated carbon, etc. The nickel content can be as high as 80%. Certain catalysts which are useful for the invention can be formed of droplets of nickel powder linked by an amine. The alkaline carbonate/Ni +Cu systems are also part of the invention. Use is preferably made of this type of catalyst with a Ni:Cu weight ratio between 100:1 and 10:1.

The catalysts in accord with the invention are used in amounts between 1 and 15% by weight, preferably between 2 and 7%, in relation to the fatty chain reactant employed. Preference is given to the products cited in the examples below, which include HARSHAW catalyst Ni 1404 T which contains 60% of nickel deposited on kieselguhr, Ni 5189D which contains 18% by weight of Ni, 2% by weight of Cu, and 7% by weight of a support, preferably alumina made into a paste with distearylamine (if a fatty alcohol is used in the reaction it can also be used to form the paste), MALLINCK- RODT catalyst E 230 P which contains 60% by weight nickel deposited on aluminum, MALLINCKRODT E 480 P which contains 65% by weight of supported nickel, or GIRDLER catalyst G96 which contains 23% by weight of nickel deposited on silica (6.5% by weight) and formed into a paste with distearylamine.

In all cases, the Ni/support+alkaline carbonate (particularly $K_2CO_3$) catalytic system makes it possible to limit the dimethylated tertiary $RN(CH_3)_2$ content of the resultant amination product to less than 2% and the dialkylated amine (which can be subsequently separated out by distillation) content to less than 6%. This selectivity is a characteristic of the present invention.

EXAMPLES

The examples below will provide for better comprehension of the invention and its advantages. In the description of the examples, the amounts of catalyst and alkaline carbonate are always expressed as weight percent in relation to the initial heavy amine or heavy alcohol (10/22 carbon atoms).

EXAMPLES 1 and 2

Production of N-methyl-N-dodecylamine from Dodecylamine and Methanol

The operating procedure described above is followed with the following specific conditions: a hydrogen pressure of 40 bars and agitation of 1800 rpm for 6 hours at 180° C. The following reactants were introduced into the autoclave for Test No. 1:

(i) 422 g of dodecylamine (2.3 moles),
(ii) 1460 g of methanol (45 moles),
(iii) 38.6 g of HARSHAW catalyst Ni 1404 T, and
(iv) 57.1 g of $K_2CO_3$.

A comparative example (Test No. 2) was carried out under the same conditions, but without introduction of potassium carbonate. Table I below shows the results.

TABLE I

| Test | $K_2CO_3$ | Reaction Products (weight expressed as percentage) | | | | |
|---|---|---|---|---|---|---|
| | | $RNH_2$ | $RHNCH_3$ | $RN(CH_3)_2$ | $R_2NH$ | ROH |
| 1 | yes | — | 85.9 | 1.3 | 6.0 | 6.8 |
| 2 | no | 15.0 | 17.2 | 44.9 | 13.8 | 9.1 |

These results demonstrate clearly that the presence of $K_2CO_3$ in the medium makes possible the selective formulation of N-methyl-dodecylamine and that it increases the activity of the catalyst.

EXAMPLES 3 to 5

Production of N-methyldodecylamine from Dodecylamine and Methanol

Table II shows the results for three tests carried out with the methanol:amine molar ratio (referred to below as M:A) varied between 5 and 15 under 40 bars of hydrogen at 180° C. for 6 hours in the presence of 9.1% of HARSHAW catalyst Ni 1404 T and 13.5% of $K_2CO_3$, compared to Example 1 in which the M:A ratio was 20.

TABLE II

| Test | M:A | Reaction Products (weight expressed as percentage) | | | | |
|---|---|---|---|---|---|---|
| | | $RNH_2$ | $RHNCH_3$ | $RN(CH_3)_2$ | $R_2NH$ | ROH |
| 3 | 5 | 46.7 | 48.2 | 0.8 | 2.4 | 2.5 |
| 4 | 10 | 17.1 | 75.4 | 0.3 | 3.8 | 3.8 |
| 5 | 15 | 05.6 | 82.4 | 1.7 | 5.5 | 4.8 |
| 1 | 20 | — | 85.9 | 1.3 | 6.0 | 6.8 |

These examples demonstrate the influence of the molar ratio M:A of methanol to the monomethylamine; increasing this ratio improves the methylation activity without exceeding 2% of dimethyldodecylamine.

EXAMPLES 6 to 10

Table III shows the results for the preparation of N-ethyldodecylamine (Test No. 6), N-isopropyldodecyl amine (Test No. 7), N-methylalkyl(copra)amine (Test No. 8), N-methylalkyl(tallow)amine (Test No. 9) and N-methyl-alkyl(C20/C22)amine (Test No. 10) from fatty amines and the corresponding light alcohols. In the table, the symbol R indicates heavy chains (C12-copra, tallow,C20/22) and the symbol R′ indicates short chains (C1/C3).

The tests were performed with the raw materials listed in Table III in the presence of HARSHAW catalyst Ni 1404 T and $K_2CO_3$ at 180° C. under 50 bars of hydrogen. The alcohol:amine molar ratio was maintained at 10. The table shows that the $RN(R')_2$ amine content remains lower than 2% by weight no matter what initial reactants are used.

TABLE III

| Test | Reactants | Catalyst wt. % | $K_2CO_3$ wt. % | Reaction time (h) | Reaction Products (by weight) | | | |
|---|---|---|---|---|---|---|---|---|
| | | | | | $RNH_2$ | RNHR′ | $RN(R')_2$ | $R_2NH$ + ROH |
| 6 | dodecylamine + ethanol | 9.2 | 13.5 | 19.0 | 1.9 | 66.0 | 1.9 | 30.2 |
| 7 | dodecylamine + isopropanol | 9.2 | 13.5 | 19.0 | 2.3 | 90.0 | 0.5 | 7.2 |
| 8 | copra amine + methanol | 7.7 | 11.3 | 06.5 | 24.0 | 64.0 | 1.2 | 10.8 |
| 9 | tallow amine + methanol | 5.7 | 6.3 | 26.0 | 2.3 | 84.0 | 1.5 | 12.2 |
| 10 | C20/C22 amine + methanol | 5.7 | 8.3 | 15.0 | 9.7 | 69.0 | 1.7 | 19.6 |

EXAMPLES 11 to 18

Table IV shows the results for the preparation of N-methyldodecylamine from dodecylamine and methanol according to the conditions employed in Example 1, but employing lithium, sodium or potassium carbonate in varying proportions.

These examples demonstrate that the presence of alkaline carbonate promotes the selective formation of N-methyldodecylamine and that this effect is most pronounced with $K_2CO_3$.

TABLE IV

| Test | Additive Type | wt. %/amines | Reaction Products (weight expressed as %) | | | |
|---|---|---|---|---|---|---|
| | | | $RN(CH_3)_2$ | $RNHCH_3$ | $R_2NH$ | not determined |
| 11 | $Li_2CO_3$ | 1 | 14 | 31 | 42 | 13 |
| 12 | $Li_2CO_3$ | 10 | 10 | 28 | 21 | 41 |
| 13 | $Na_2CO_3$ | 5 | 21 | 55 | 6 | 18 |
| 14 | $Na_2CO_3$ | 10 | 55 | 39 | 2 | 4 |
| 15 | $Na_2CO_3$ | 15 | 12 | 60 | 17 | 11 |
| 16 | $K_2CO_3$ | 5 | 3 | 32 | 61 | 4 |
| 17 | $K_2CO_3$ | 10 | 2 | 80 | 0 | 18 |
| 18 | $K_2CO_3$ | 15 | 2 | 78 | 2 | 18 |

EXAMPLES 19 and 20

Table V shows the results for the preparation of N-methyl-alkyl(C12/14)amines from fatty alcohol and monomethylkamine according to the previously described general operating procedure in which 466 g of C12/C14 cut alcohols (75% dodecanol/25% tetradecanol) were charged; 5% of supported nickel catalyst in relation to the alcohol and 5% of potassium carbonate in relation to the alcohol were employed. The pressure was 10 bars, the hydrogen flow rate was 100 L/hour, the monomethylamine flow rate was 40 g/hour and the total duration of operations was 7 hours.

These examples clearly demonstrate the specific effect of the additive $K_2CO_3$ for the selectivity of the synthesis of N-methyl-alkylamines.

TABLE V

| Test | Catalyst | Temp. °C. | Conversion ROH (wt. %) | $RNH_2$ | $RNHCH_3$ | $RN(CH_3)_2$ | dialkyl-amines | trialkyl-amines |
|---|---|---|---|---|---|---|---|---|
| 19 | Ni 1404 T (alone) | 200 | 100 | 1.4 | 3 | 0 | 68.3 | 27.3 |
| 20 | Ni 1404 T + $K_2CO_3$ | 200 | 75.4 | 6.8 | 72.7 | 2.5 | 17.1 | 0.9 |

EXAMPLES 21 to 25

Table VI shows the results of the preparation of N-methyldodecylamine from dodecanol and monomethylamine according to the previously described general operating procedure in which 433 g of dodecanol was charged; 5% of supported nickel catalyst in relation to the alcohol and 2.5% of potassium carbonate in relation to the alcohol were employed. The selected temperature was 200° C., the hydrogen flow rate was 100 L/hour, the monomethylamine flow rate was 26 g/hour and the total duration of operations was 7 hours. The pressure was 10 bars.

TABLE VI

| Test | Catalyst | Conversion ROH (wt. %) | $RNH_2$ | $RNHCH_3$ | $RN(CH_3)_2$ | dialkyl-amines | trialkyl-amines |
|---|---|---|---|---|---|---|---|
| 21 | Ni 1404 T | 75 | 6.8 | 72.7 | 2.5 | 17.1 | 0.9 |
| 22 | Ni 8849 D + $K_2CO_3$ | 68 | 2.3 | 85.1 | 0.2 | 9.9 | 2.5 |
| 23 | E 230 P + $K_2CO_3$ | 84 | 1.2 | 75.4 | 1.1 | 22.1 | 0.2 |
| 24 | G 96 + $K_2CO_3$ | 69 | 1.0 | 93.9 | 0.1 | 5.0 | 0 |
| 25 | E 480 P + $K_2CO_3$ | 85 | 0.4 | 75.8 | 2.4 | 21.4 | 0 |

EXAMPLES 26 to 28

Table VII shows the results for the preparation of N-methyldodecylamine from dodecanol and monomethylamine according to the operating procedure and conditions employed by Examples 21 to 25 with the only changes being variation of the total hydrogen pressure between 3 and 30 bars and use of Ni 5189 D catalyst

TABLE VII

| Test | $H_2$ pressure (bars) | Conversion ROH (wt. %) | Selectivity (weight expressed as %) | | | |
|---|---|---|---|---|---|---|
| | | | $RNH_2$ | $RNHCH_3$ | $RN(CH_3)_2$ | dialkylamines |
| 26 | 3 | 61 | 2.6 | 73.1 | 1.7 | 22.3 |
| 27 | 10 | 59 | 3.7 | 89.3 | 0.5 | 4.6 |
| 28 | 30 | 50 | 3.6 | 90.4 | 1.0 | 2.4 |

The example demonstrates the very favorable influence of hydrogen which prevents the massive formation of dialklyamines.

EXAMPLES 29 to 31

Table VIII shows the results for the preparation of N-methyldodecylamine from dodecanol and monomethylamine according to the operating procedure and conditions of Examples 21 to 25 with the pressure set at 10 bars, the temperature at 200° C. and the monomethylamine flow rate at 26 g/hour. Unlike Examples 21 to 25, the catalyst was added twice during the operation and, as shown in Table VIII, the total duration of the reaction exceeded 7 hours. In this manner, there was produced a product responding to the general specifications of dimethylated amine and primary amine content with a conversion rate greater than 98%.

TABLE VIII

| Test | Catalyst Type | Wt.-% | $K_2CO_3$ wt.-% | Reaction time (h) | ROH converted (wt.-%) | $RNH_2$ | $\underset{CH_3}{RNH}$ | $\underset{CH_3}{\overset{CH_3}{RN}}$ | dialkylamines | trialkylamines |
|---|---|---|---|---|---|---|---|---|---|---|
| 29 | Ni 8849 L | 5 | 0.6 | 7 | 61 | 3.1 | 87.4 | 0 | 9.5 | 0 |
|  |  | +5 | +0.6 | +7 | 98 | 2.5 | 78.1 | 1.5 | 16.3 | 1.6 |
| 30 | E 480 P | 2.5 | 1.25 | 7 | 71 | 0.4 | 88.1 | 0.1 | 11.4 | 0 |
|  |  | +2.5 | +1.25 | +7 | 99 | 0.4 | 76.1 | 2.5 | 21.0 | 0 |
| 31 | E 230 P | 2.5 | 1.25 | 7 | 68 | 0.1 | 82.3 | 0.2 | 17.4 | 0 |
|  |  | +2.5 | +1.25 | +7 | 99 | 0.4 | 83.5 | 1.7 | 14.4 | 0 |

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A process for the preparation of secondary methylalkyl amines of general formula:

$$R-NH-CH_3$$

in which R is $C_{10}-C_{22}$ aliphatic chain, by amination reaction between an alcohol and a monoalkylamine comprising carrying out said amination reaction by catalysis with a supported nickel catalyst in the presence of potassium carbonate, the weight ratio between the potassium carbonate and the nickel catalyst being between 1:4 and 1:1, under a hydrogen pressure between 10 and 50 bars.

2. The process of claim 1, wherein the amination reaction is performed between a fatty alcohol with 10 to 22 carbon atoms and monomethylamine.

3. The process of claim 1, wherein the amination reaction is performed between a fatty monoamine with 10 to 22 carbon atoms and methanol.

4. The process of claim 1, wherein the catalyst is a mixed nickel/copper catalyst.

5. The process of claim 3 wherein the methanol is introduced in an amount such that the molar ratio between the methanol and the amine is between 15 and 30.

6. The process of claim 2, wherein the molar ratio between the monomethylamine and the fatty alcohol is between 1 and 5.

7. The process of claim 1, wherein the amount of catalyst is between 1 and 15% by weight in relation to the fatty chain reactant employed.

8. The process of claim 2, wherein the amount of catalyst is between 1 and 15by weight in relation to the fatty chain reactant employed.

9. The process of claim 3, wherein the amount of catalyst is between 1 and 15% by weight in relation to the fatty chain reactant employed.

* * * * *

UNITED STATES PATENT AND TRADEMARK OFFICE
CERTIFICATE OF CORRECTION

PATENT NO. : 5,254,736
DATED : October 19, 1993
INVENTOR(S) : Forquy Christian

It is certified that error appears in the above-indentified patent and that said Letters Patent is hereby corrected as shown below:

Column 10, Claim 8, line 2, cancel "15by" and substitute therefor-- 15% by--

Signed and Sealed this

Twenty-second Day of February, 1994

Attest:

BRUCE LEHMAN

*Attesting Officer*   *Commissioner of Patents and Trademarks*